United States Patent
Ellingson et al.

(10) Patent No.: US 11,378,638 B2
(45) Date of Patent: Jul. 5, 2022

(54) MULTI-ECHO SPIN-, ASYMMETRIC SPIN-, AND GRADIENT-ECHO ECHO-PLANAR IMAGING MRI PULSE SEQUENCE

(71) Applicant: The Regents of the University of California, Oakland, CA (US)

(72) Inventors: Benjamin Ellingson, Los Angeles, CA (US); Kevin Leu, Los Angeles, CA (US)

(73) Assignee: The Regents of the University of California, Oakland, CA (US)

(*) Notice: Subject to any disclaimer, the term of this patent is extended or adjusted under 35 U.S.C. 154(b) by 316 days.

(21) Appl. No.: 15/754,239

(22) PCT Filed: Aug. 29, 2016

(86) PCT No.: PCT/US2016/049193
§ 371 (c)(1),
(2) Date: Feb. 21, 2018

(87) PCT Pub. No.: WO2017/040368
PCT Pub. Date: Mar. 9, 2017

(65) Prior Publication Data
US 2018/0252789 A1  Sep. 6, 2018

Related U.S. Application Data

(60) Provisional application No. 62/211,852, filed on Aug. 30, 2015.

(51) Int. Cl.
*G01R 33/561* (2006.01)
*G01R 33/48* (2006.01)
(Continued)

(52) U.S. Cl.
CPC ........ *G01R 33/5616* (2013.01); *A61B 5/0042* (2013.01); *A61B 5/055* (2013.01);
(Continued)

(58) Field of Classification Search
CPC ..... A61B 5/0042; A61B 5/055; A61B 5/4064; A61B 5/407; G01R 33/4806; G01R 33/50;
(Continued)

(56) References Cited

U.S. PATENT DOCUMENTS 6,169,398 B1   1/2001   Watanabe
6,804,546 B1  10/2004   Thompson
(Continued)

FOREIGN PATENT DOCUMENTS

WO   2015119328   8/2015

OTHER PUBLICATIONS

Nana et al (Single-Shot Multiecho Parallel Echo-Planar Imaging (EPI) for Diffusion Tensor Imaging (DTI) With Improved Signal-to-Noise Ratio (SNR) and Reduced Distortion, Magnetic Resonance in Medicine 60:1512-1517 (2008)) (Year: 2008).*
(Continued)

*Primary Examiner* — Pascal M Bui Pho
*Assistant Examiner* — Alexei Bykhovski
(74) *Attorney, Agent, or Firm* — Quarles & Brady LLP

(57) ABSTRACT

An echo planar imaging technique in which a quadruple echo gradient and spin echo echo-planar imaging pulse sequence is utilized. The pulse train includes generation of two echo trains between an excitation pulse (90) and a refocusing pulse (180) to achieve two gradient echo images (also called T2*-weighted images); with one echo train directly after the 180 pulse, leading to asymmetric spin echo images (T2'-weighted images); and a last echo train afterward that generates spin echo images (T2-weighted). The technique has a number of advantages over existing techniques with regard to voxel size, mapping relative oxygen extraction, determining permeability, determining relative cerebral blood volume, vessel parameters (diameter, density, size, arterial/venous, etc.), stroke imaging, imaging perfusion, fMRI imaging, and additional benefits.

15 Claims, 10 Drawing Sheets

(51) Int. Cl.
*G01R 33/50* (2006.01)
*A61B 5/00* (2006.01)
*A61B 5/055* (2006.01)
*G01R 33/56* (2006.01)
*G01R 33/563* (2006.01)

(52) U.S. Cl.
CPC ......... *G01R 33/4806* (2013.01); *G01R 33/50* (2013.01); *G01R 33/5617* (2013.01); *A61B 5/407* (2013.01); *A61B 5/4064* (2013.01); *G01R 33/5602* (2013.01); *G01R 33/56366* (2013.01)

(58) Field of Classification Search
CPC ............ G01R 33/5602; G01R 33/5616; G01R 33/5617; G01R 33/56366
See application file for complete search history.

(56) References Cited

U.S. PATENT DOCUMENTS

| | | | |
|---|---|---|---|
| 2006/0001424 A1 | 1/2006 | Harvey | |
| 2010/0123460 A1 | 5/2010 | Hughes | |
| 2011/0018537 A1* | 1/2011 | Warntjes | G01R 33/50 324/309 |
| 2011/0103657 A1* | 5/2011 | Kang | A61B 6/504 382/128 |
| 2011/0196224 A1 | 8/2011 | Stehning | |
| 2014/0316218 A1* | 10/2014 | Purdon | A61B 5/0261 600/301 |

OTHER PUBLICATIONS

Zhang et al (Correlation of Volume Transfer Coefficient Ktrans with Histopathologic Grades of Gliomas, Magn Reson Imaging. Aug. 2012; 36(2): 355-363) (Year: 2012).*

Emblem, Kyrre E., et al. "Vessel architectural imaging identifies cancer patient responders to anti-angiogenic therapy." Nature medicine 19.9 (2013): 1178.

International Search Report and Written Opinion for application PCT/US2016/049193, dated Nov. 21, 2016, 9 pages.

Schmainda, Kathleen M., et al. "Characterization of a first-pass gradient-echo spin-echo method to predict brain tumor grade and angiogenesis." American Journal of Neuroradiology 25.9 (2004): 1524-1532.

Schmiedeskamp, Heiko, et al. "Combined spin-and gradient-echo perfusion-weighted imaging." Magnetic resonance in medicine 68.1 (2012): 30-40.

Schmiedeskamp, Heiko, et al. "Simultaneous perfusion and permeability measurements using combined spin-and gradient-echo MRI." Journal of Cerebral Blood Flow & Metabolism 33.5 (2013): 732-743.

Skinner, Jack T., et al. "Evaluation of a multiple spin-and gradient-echo (SAGE) EPI acquisition with SENSE acceleration: applications for perfusion imaging in and outside the brain." Magnetic resonance imaging 32.10 (2014): 1171-1180.

Stokes, Ashley M., et al. "A simplified spin and gradient echo approach for brain tumor perfusion imaging." Magnetic resonance in medicine 75.1 (2016): 356-362.

Stokes, Ashley M., et al. "Assessment of a combined spin-and gradient-echo (SAGE) DSC-MRI method for preclinical neuroimaging." Magnetic resonance imaging 32.10 (2014): 1181-1190.

Tropres, I., et al. "In vivo assessment of tumoral angiogenesis." Magnetic Resonance in Medicine: An Official Journal of the International Society for Magnetic Resonance in Medicine 51.3 (2004): 533-541.

Wu, Ed X., et al. "Applications of ultrasmall superparamagnetic iron oxide contrast agents in the MR study of animal models." NMR in Biomedicine: An International Journal Devoted to the Development and Application of Magnetic Resonance In Vivo 17.7 (2004): 478-483.

Wu, Ed X., et al. "High-resolution MR imaging of mouse brain microvasculature using the relaxation rate shift index Q." NMR in Biomedicine: An International Journal Devoted to the Development and Application of Magnetic Resonance In Vivo 17.7 (2004): 507-512.

\* cited by examiner

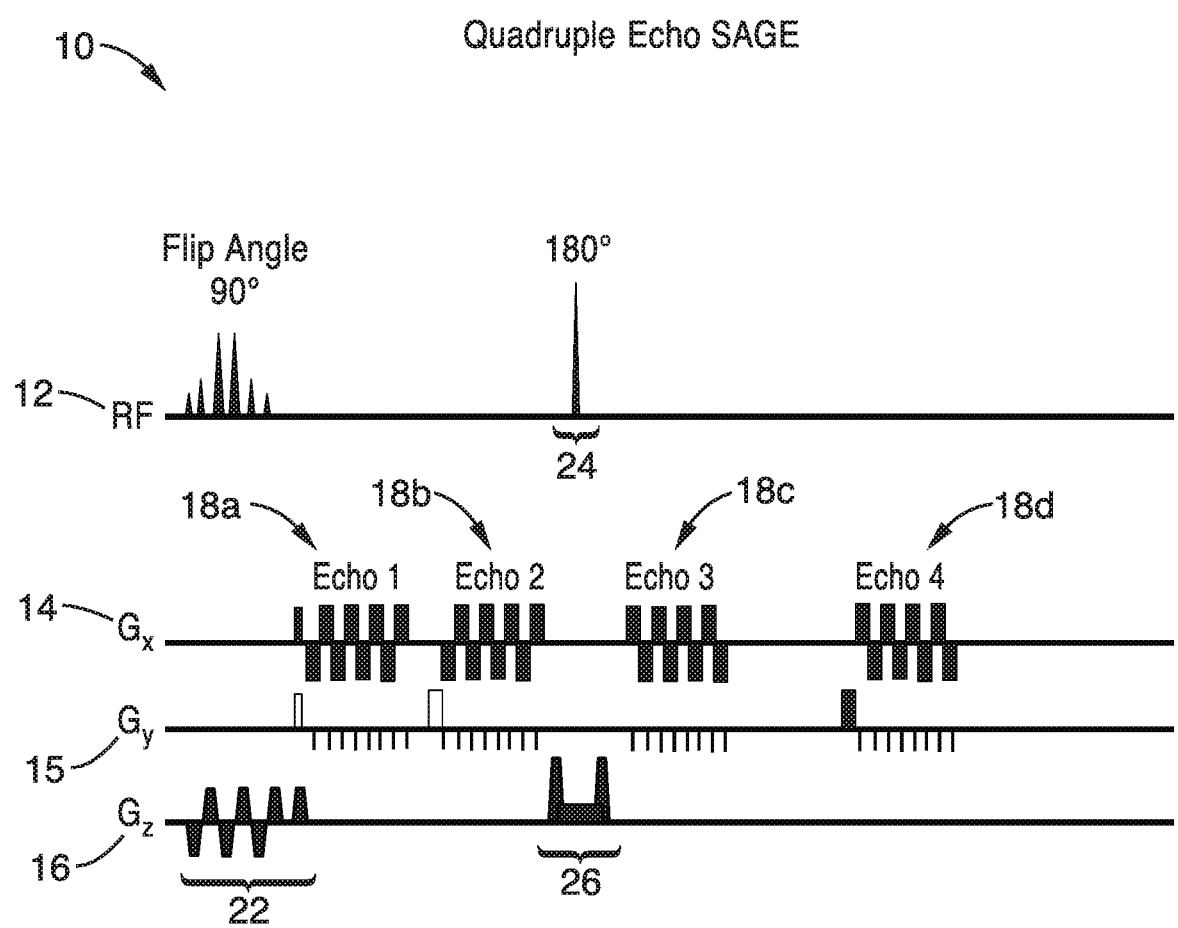
FIG. 2
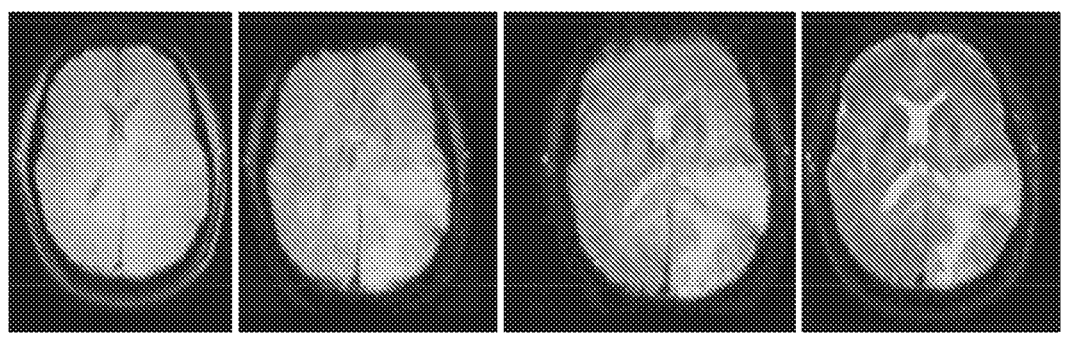
FIG. 3A    FIG. 3B    FIG. 3C    FIG. 3D

FIG. 7A  FIG. 7B  FIG. 7C
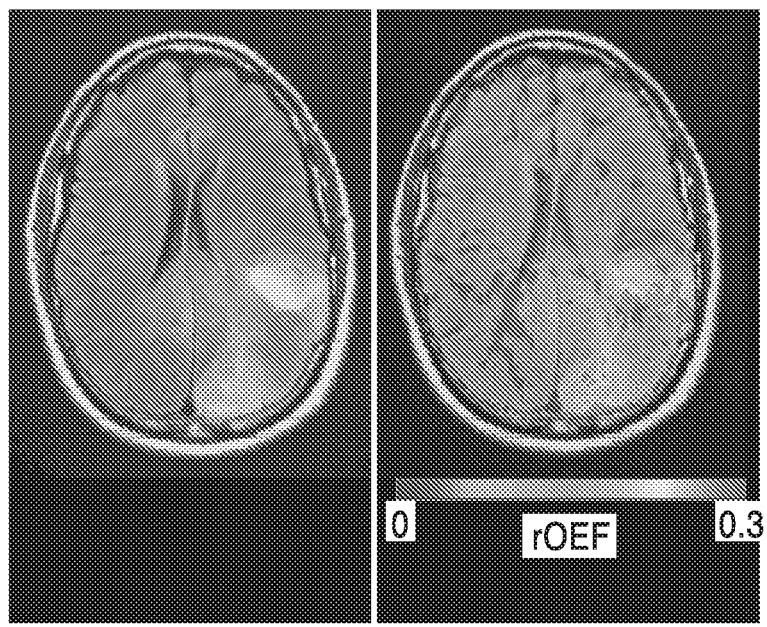
FIG. 8A  FIG. 8B

 
FIG. 9A  FIG. 9B
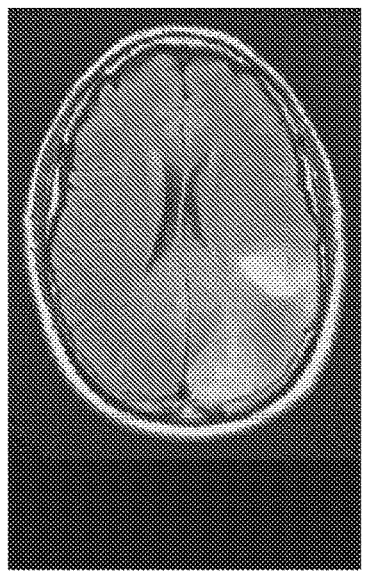 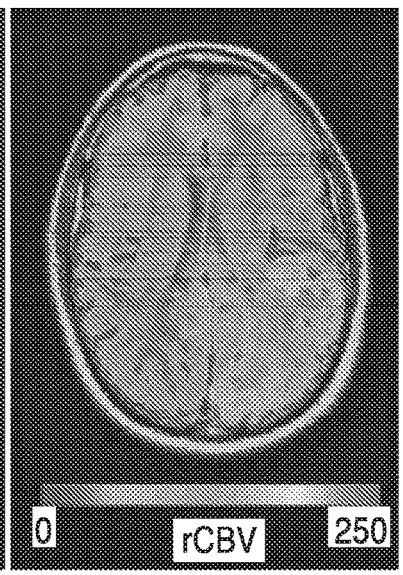 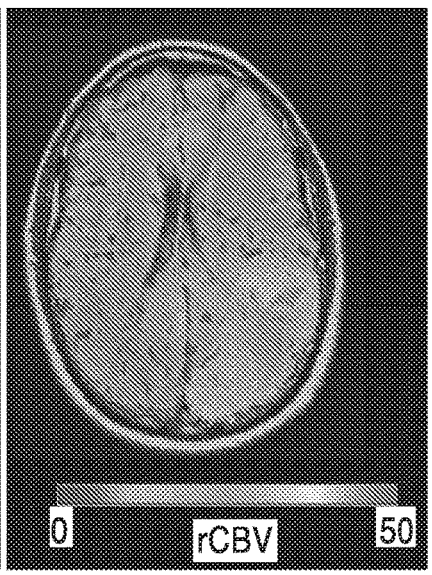
FIG. 10A  FIG. 10B  FIG. 10C

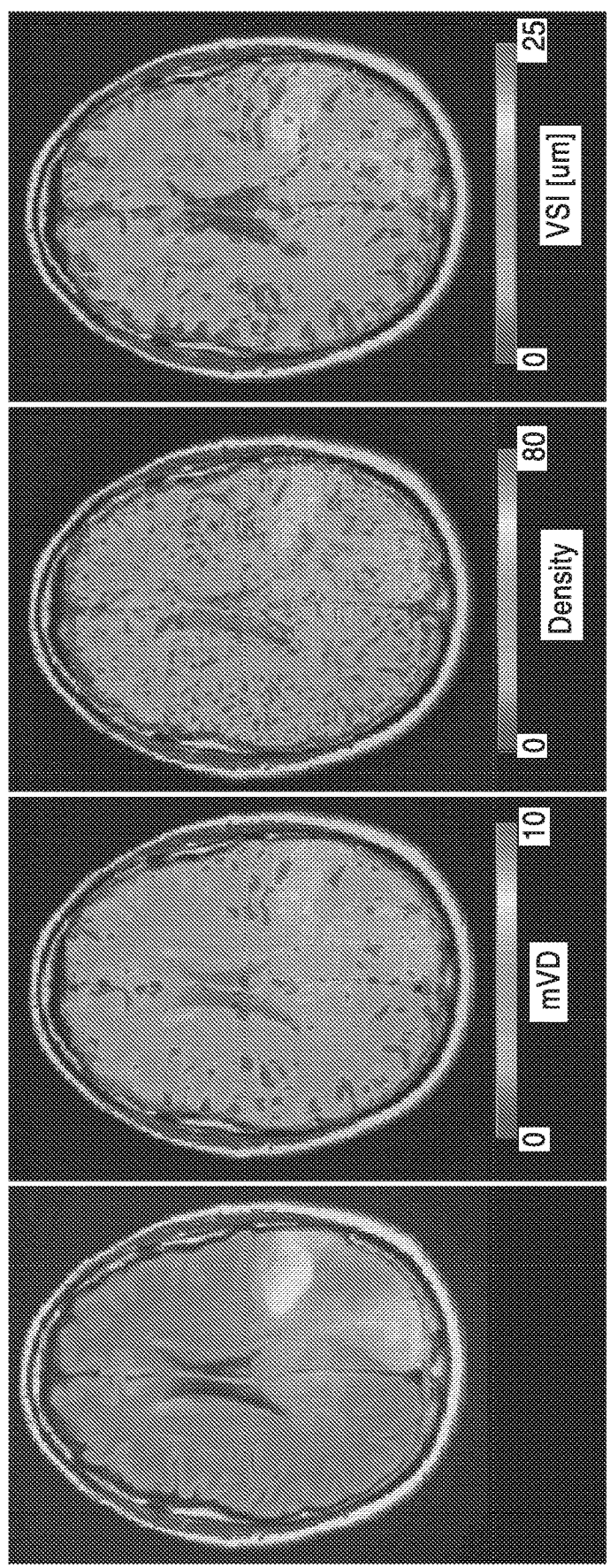

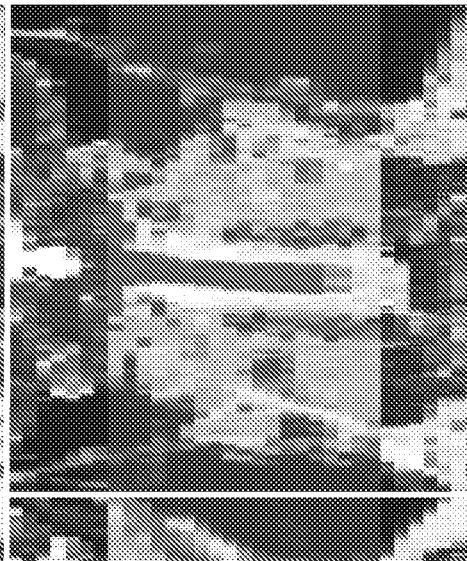
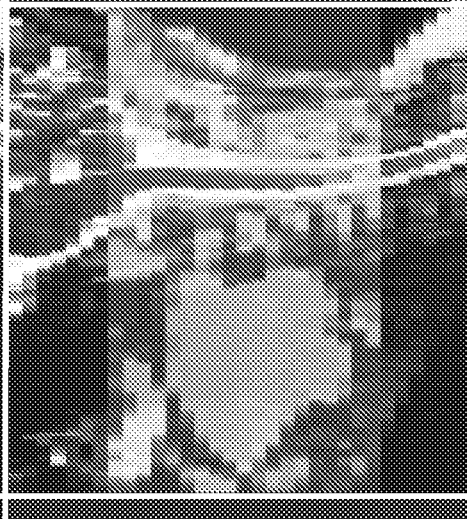
FIG. 13A  FIG. 13B  FIG. 13C
FIG. 13D  FIG. 13E  FIG. 13F echo 1 echo 2 echo 3 echo 4

MULTI-ECHO SPIN-, ASYMMETRIC SPIN-, AND GRADIENT-ECHO ECHO-PLANAR IMAGING MRI PULSE SEQUENCE

CROSS-REFERENCE TO RELATED APPLICATIONS

This application represents the national stage entry of PCT International Application PCT/US2016/049193 filed Aug. 29, 2016, which claims benefit of U.S. Provisional Application 62/211,852 filed Aug. 30, 2015, all of which is incorporated herein in its entirety by reference.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The technology of this disclosure pertains generally to echo planar imaging, and more particularly to quadruple echo gradient and spin echo echo-planar imaging pulse sequence.

2. Background Discussion

Gradient echo and spin echo single-shot echo-planar imaging (EPI) sequences have each been utilized independently in clinical magnetic resonance imaging (MRI) situations in combination with exogenous contrast agents like gadolinium to generate perfusion information in the brain, such as blood volume. EPI is the fastest acquisition method in MRI requiring only about 100 ms/slice, yet it provides limited spatial resolution. It is based on: an excitation pulse, possibly preceded by magnetization preparation.

FIG. 1A depicts a conventional gradient echo EPI sequence. For this sequence, a 90° RF pulse is played, followed by one EPI readout train per repetition time (TR), leading to $T_2^*$-weighted images. This type of sequence is more sensitive to large vessels.

FIG. 1B depicts a conventional gradient spin-echo EPI sequence. For this sequence, a 90° RF pulse is played, followed by a 180° refocusing pulse, which is succeeded by one EPI readout train per TR, leading to $T_2$-weighted images. This type of sequence is more sensitive to the microvasculature.

However, these techniques are unable to provide sufficient image resolution, and image relationships to allow extracting a number of significant characteristics from the clinical imaging situation.

Accordingly, a need exists for an improved EPI sequence and its processing, which overcomes these shortcomings. The present disclosure fulfills that needs, and provides a number of additional benefits.

BRIEF SUMMARY

An MRI pulse sequence method and apparatus are described, which enhances spin echo EPI sequences. In this technique the number of acquired echoes is increased to four echo trains, with two echo trains between the excitation pulse and refocusing pulse, and two echo trains after the refocusing pulse. The apparatus and method provides numerous benefits for improved diagnostics.

Further aspects of the technology described herein will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only:

FIG. 2 is a waveform diagram for a quadruple echo gradient and spin echo EPI sequence according to an embodiment of the present disclosure.

FIG. 3A through FIG. 3D are echo images $TE_1$ through $TE_4$, received in response to generating quadruple echo gradient and spin echo EPI sequence according to an embodiment of the present disclosure.

FIG. 7A through FIG. 7C are images from pre-bolus quantitative T2/T2* mapping generated in response to a quadruple echo gradient and spin echo EPI sequence according to an embodiment of the present disclosure.

FIG. 8A and FIG. 8B are images of relative oxygen extraction function as generated in response to a quadruple echo gradient and spin echo EPI sequence according to an embodiment of the present disclosure.

FIG. 9A and FIG. 9B are images indicating permeability as generated in response to a quadruple echo gradient and spin echo EPI sequence according to an embodiment of the present disclosure.

FIG. 10A through FIG. 10C are images showing relative cerebral blood volume as generated in response to a quadruple echo gradient and spin echo EPI sequence according to an embodiment of the present disclosure.

FIG. 11A through FIG. 11D are images showing various vessel parameters generated in response to a quadruple echo gradient and spin echo EPI sequence according to an embodiment of the present disclosure.

FIG. 13A through FIG. 13F are images of spinal cord perfusion as generated in response to a quadruple echo gradient and spin echo EPI sequence according to an embodiment of the present disclosure.

DETAILED DESCRIPTION

Figure 1A:
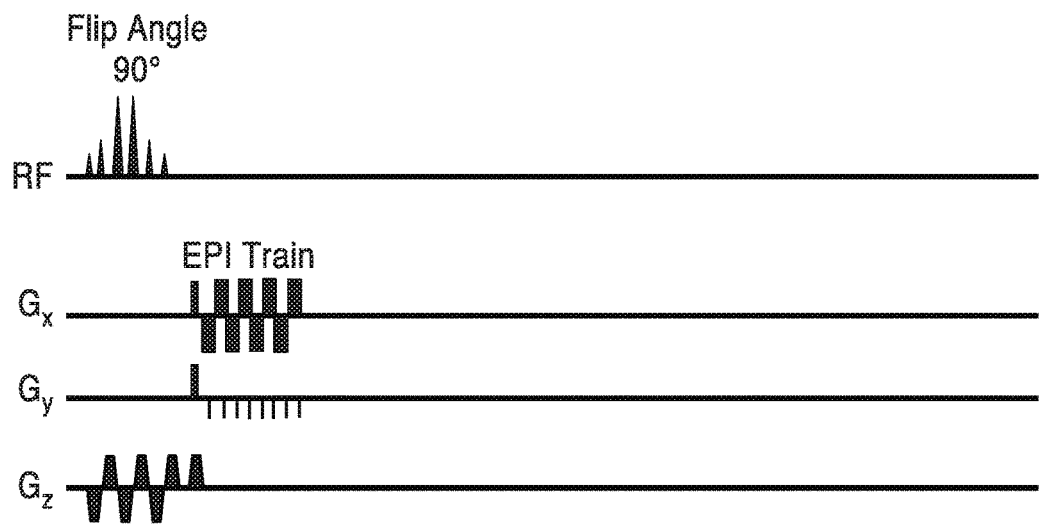
FIG. 1A and FIG. 1B are waveform diagrams of conventional gradient echo, and spin echo EPI sequences.
Figure 1B:
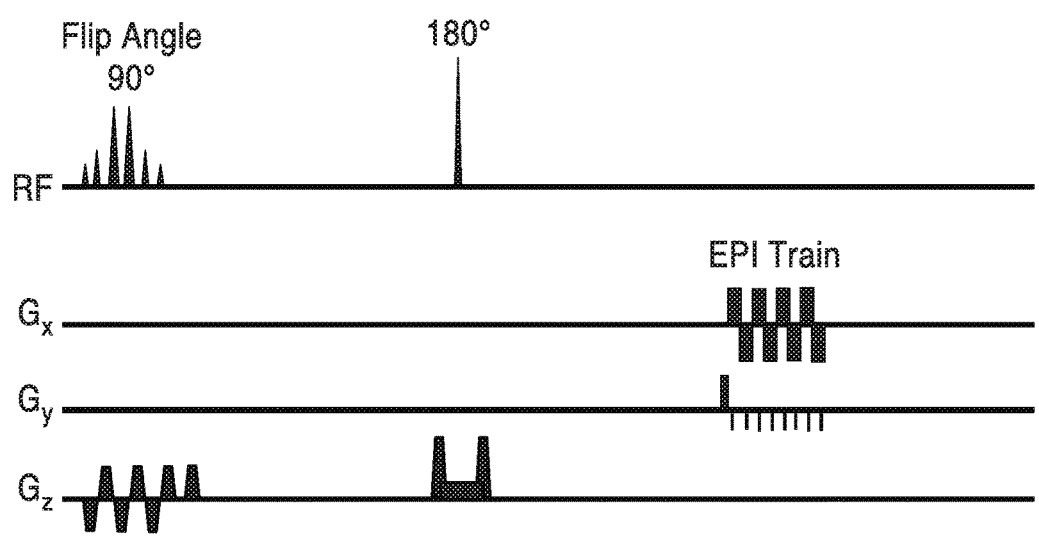
Figures 4A, 4B, 4C, 4D:
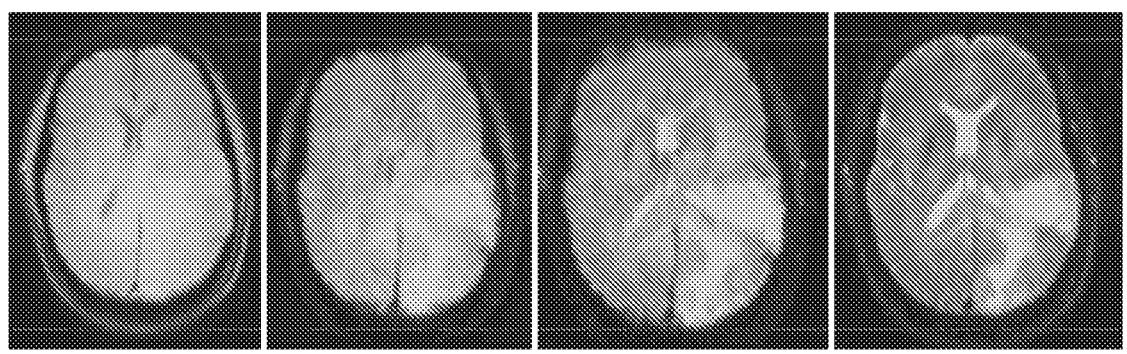
FIG. 4A through FIG. 4D are echo images for prebolus baseline generated in response to a quadruple echo gradient and spin echo EPI sequence according to an embodiment of the present disclosure.
Figures 5A, 5B, 5C, 5D:
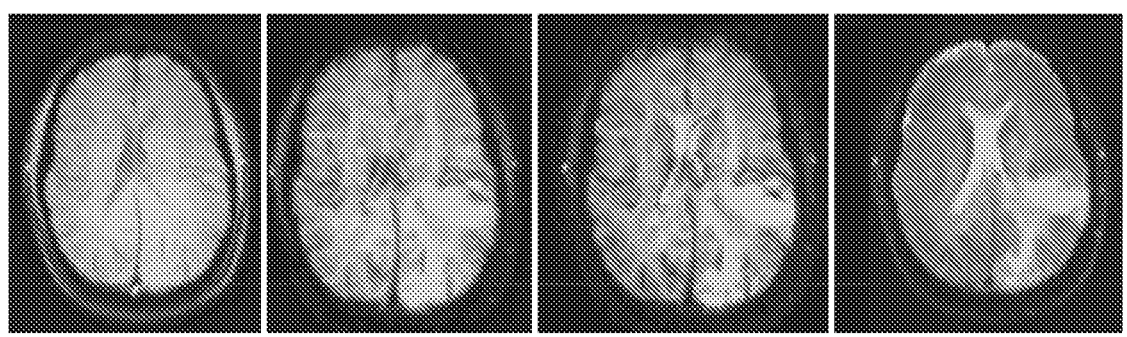
FIG. 5A through FIG. 5D are echo images for peak bolus passage generated in response to a quadruple echo gradient and spin echo EPI sequence according to an embodiment of the present disclosure.

1. Introduction.

A quadruple echo gradient and spin echo EPI sequence is disclosed which provides numerous benefits. This spin echo technique can currently be performed at field strengths of 3 T (Tesla) in humans, while it is expected that the techniques can be applied at other field strengths (e.g., lower or higher) in both humans and preclinical (animal) models.

2. Quadruple Echo Gradient and Spin Echo EPI Sequence.

FIG. 2 illustrates an example embodiment 10 of a quadruple echo gradient and spin echo EPI MRI pulse sequence using the RF pulse, $G_x$, $G_y$, and $G_z$ gradient coils (elements 12, 14, and 16) which is a modified version of the spin echo EPI sequence. In particular, the number of acquired echoes has been increased from one echo train to four echo trains, with two echo trains between an excitation pulse (90°) (elements 20 and 22) and the refocusing pulse (180°) with spoiler gradient (elements 24 and 26) to achieve two gradient echo images (also called T2*-weighted images) (elements 18a and 18b), one echo train directly after the 180° pulse, leading to asymmetric spin echo images (T2'-weighted images) (element 18c), and one last echo that generates the spin echo images (T2-weighted) (element 18d).

FIG. 3A through FIG. 3D illustrate different signal intensities generated from the four different echoes at $TE_1$ through $TE_4$, respectively. Each scan accordingly yields four images, each with different contrasts available to enhance analysis. In FIG. 3A the image is from the first echo at 14.0 ms (T2* weighted), in FIG. 3B the image is from the second echo at 34.1 ms (T2* weighted), in FIG. 3C the image is from the third echo at 58.0 ms (T2' weighted), and in FIG. 3D the image is from the fourth echo at 92.4 ms (T2 weighted). With parallel imaging reduction factor of 3, partial Fourier 6/8, can achieve matrix size ($k_x \times k_y$) of 128×104 for an in-plane resolution of 1.875×1.875 mm. This voxel size matches the typical size of a clinical perfusion scan from either the conventional gradient or spin echo sequences, with the added bonus of being to compute many more biomarkers than the conventional scans. Table 1 summarizes these parameters for the images shown.

The disclosure is particularly well-suited for use in brain tumor scanning, although it may be utilized without limitation in other clinical and non-clinical applications.

3. Benefits of Disclosed Quadruple Echo EPI Sequence.

The disclosed quadruple echo gradient and spin echo EPI sequence provides a number of advantages over other multi-echo sequences in brain tumors.

3.1 Reduced Voxel Size.

In order to measure hypoxia in brain tumors, the system determines quantitative T2 and T2* measures. As stipulated by Eq. 1 (below), there are four unknowns: R2*, R2, δ, and $S_0$. Therefore, to solve for each unknown, four images with different MR characteristics or "contrasts" must be acquired simultaneously. The advent of a three-echo EPI sequence does not allow for the quantitative calculation of T2, and therefore, would not allow us to calculate $R_2'$ and oxygen extraction fraction. The advent of the five-echo version pushes the last echo to echo times that are too long to gain adequate signal relative to noise, unless the voxel resolution is reduced. Furthermore, the proposed 5-echo versions provides a minimum of a 2.857×2.857 mm in-plane resolution, which is a voxel size too large to be used for perfusion scans clinically, whereas the four-echo version allows reduction of the voxel size to 1.875×1.875 mm, which is the same size as the typical gradient echo EPI perfusion-weighted used for clinical purposes.

3.2 Quantitative T2/T2* Mapping and Relative Oxygen Extraction Fraction.

The disclosed quadruple echo gradient and spin echo EPI sequence provides the ability to compute quantitative T2, T2*, or R2'; because there are two echoes that are T2*-weighted, quantitative T2* can be obtained.

Figure 6:
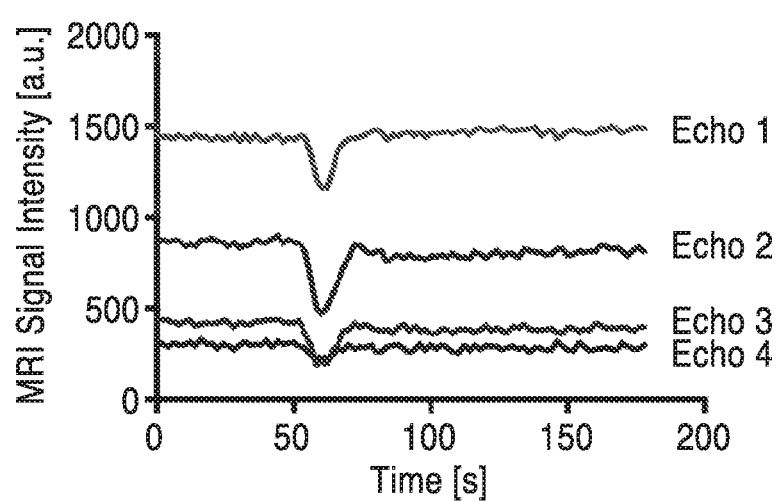
FIG. 6 is a plot of MRI signal intensity for echoes from a quadruple echo gradient and spin echo EPI sequence according to an embodiment of the present disclosure.

FIG. 4A through FIG. 7 illustrate echo outputs (Echo 1 through Echo 4) for both pre-bolus baseline images (FIG. 4A through FIG. 4D), and for images acquired at peak bolus passage (FIG. 5A through FIG. 5D). MRI signal intensity is seen in FIG. 6 for each of the four echoes. While FIG. 7A through FIG. 7C depict pre-bolus quantitative T2/T2* mapping. It should be appreciated that this can only be achieved by using a minimum of four echoes as the equation below has four unknowns. As stated before, the use of four echoes, the minimum required, allows for spatial resolution that matches that of the typical perfusion-weighted MRI.

FIG. 7A through FIG. 7C illustrate pre-bolus quantitative T2/T2* mapping. In FIG. 7A FLAIR is shown which is from a conventional anatomical scan, and which was not acquired by the disclosed pulse sequence but used to indicate the location of the tumor. It is standard practice in the MRI literature to include a conventional anatomical scan side-by-side with results from new MRI techniques so that people can easily locate the tumor lesion.

A T2 map is seen in FIG. 7B, and T2* map in FIG. 7C, as acquired using the disclosed pulse sequence. The two T maps together allows us to calculate R2', which is a measurement that is proportional to the degree of hypoxia.

$$S(t) = \begin{cases} S_0 e^{-t \cdot R2^*}, & t = \{TE_1, TE_2\} \\ S_0/\delta \cdot e^{-t(R2^*-R2)} e^{-t(2 \cdot R2 - R2^*)}, & t = \{TE_3, TE_4\} \end{cases} \quad (1)$$

wherein R2*=1/T2* (quantitative), R2=1/T2 (quantitative), $S_0$ is a scaling factor corresponding to spin density, and δ is a variable accounting for slice imperfections in the asymmetric and spin echoes.

FIG. 8A through FIG. 8B illustrate that by dividing R2' by relative cerebral blood volume, a determination of rOEF (relative oxygen extraction fraction) can be made indicating the degree of oxygen usage by the brain.

$$rOEF = (R2^* - R2)/rCBV \quad (2)$$

The above abilities are distinct from those of three-echo techniques which are unable to obtain quantitative T2 or R2' since Eq. 1 requires a minimum of four echoes. Metabolic demand in brain tissues is the result of a coupling between perfusion and oxygen demand. In brain tumors, perfusion (i.e., blood flow) is much higher, so the brain tumor's oxygen demands are lower. We therefore expect brain tumors to demonstrate low rOEF since tumor tissues tend to exhibit weak oxygen metabolism as compared to normal brain tissue.

3.3 Permeability.

The disclosed quadruple echo gradient and spin echo EPI sequence also provides permeability advantages over existing dual gradient-and-spin echo sequences. The configuration for using four echoes allows the disclosed device to determine a baseline T1-weighted image ($S_0$) that can be combined with a T1 map and two-compartment pharmacokinetic modeling of contrast agent exchange to determine the forward transfer coefficient, $K^{trans}$, a biomarker that is related to the permeability of the vasculature in brain tumors.

FIGS. 9A and 9B illustrate an example of the above exchange advantage, by showing permeability, which requires a minimum of four echoes to calculate. Calculating permeability first requires the calculation of $S_0$ from section related to Eq. 1, which is T1-weighted, then requires a fit to the following equation:

$$S_0(t) = \frac{S_{0,baseline}\left(1 - \exp\left(-TR\left(\frac{1}{T_{10}} - r_1 c_T(t)\right)\right)\right)}{1 - \exp\left(-\frac{TR}{T_{10}}\right)} \quad (3)$$

where $S_0$ is the signal intensity calculated from the equation in Eq. 1, $S_{0,baseline}$ is the pre-contrast signal intensity of $S_0$, TR is the repetition time, $T_{10}$ is the pre-contrast tissue $r_1$, and $c_T(t)$ is the concentration of gadolinium, the variable that the system is solving for.

3.4 Gradient and Spin Echo Relative Cerebral Blood Volume.

FIG. 10A and FIG. 10B illustrate using the disclosed quadruple echo gradient (FIG. 10A) and spin echo (FIG. 10B) EPI sequence for obtaining a gradient-echo and spin-echo version of relative cerebral blood volume. The gradient-echo rCBV is more sensitive to the passage of the bolus of contrast agent, while the spin-echo rCBV is more sensitive to the microvessels. The use of both together can yield information about vessel parameters and architecture.

It should be appreciated that these biomarkers cannot be obtained by conventional single-echo sequences.

3.5 Vessel Diameter, Density and Size.

FIG. 11A depicts a conventional T2-weighted anatomical image that demonstrates the presence and location of a tumor.

FIG. 11B through FIG. 11D illustrate that with the simultaneous acquisition of conventional gradient echo (echo 2) and spin echo (echo 4) EPI sequences, a determination can be made for mean vessel diameter (mVD) (FIG. 11B), vessel density (FIG. 11C), and vessel size (VSI) (FIG. 11D), which can be markers of tumor angiogenesis and aggressiveness.

$$mVD = \Delta R_2^* / \Delta R_2 \quad (4)$$

$$Density = 329 \cdot (\Delta R_2)^3 / (\Delta R_2^*)^2 \quad (5)$$

$$VSI = 0.424 \cdot (ADC/\gamma \Delta \chi B_0)^{1/2} (\Delta R_2^* / \Delta R_2)^{3/2} \quad (6)$$

wherein $\Delta R2^*$ is the maximum T2* relaxivity achieved per voxel by the passage of contrast agent bolus through the vasculature on the gradient echo, $\Delta R2$ is the maximum T2 relaxivity achieved per voxel on the spin echo, γ is the gyromagnetic ratio of proton, ΔX is the blood magnetic susceptibility of gadolinium, and $B_0$ is field strength.

Figure 12A:
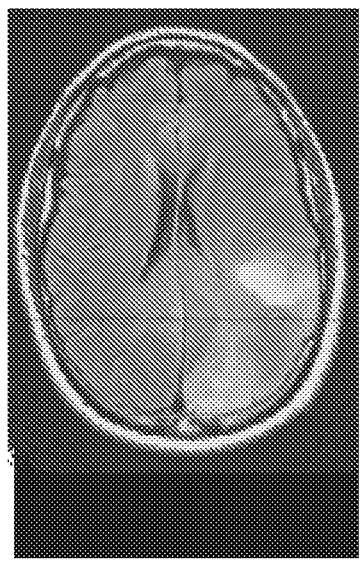
FIG. 12A through FIG. 12C are images showing a comparison between PET and MRI utilized according to an embodiment of the present technology.
Figure 12B:
Figure 12C:

FIG. 12A through FIG. 12C illustrate images generated by the disclosed technology showing a comparison between MRI vs. PET. Areas with high vessel size index (VSI), an imaging biomarker that can only be computed with the simultaneous acquisition of the spin-and-gradient echo EPI sequences, correspond with areas with high $F^{18}$-DOPA PET uptake. FIG. 12A illustrates the conventional T2-weighted anatomical imaging, which demonstrates the presence and location of a tumor. FIG. 12B demonstrates the parametric map of vessel size in micrometers, and FIG. 12C demonstrates uptake on the PET imaging modality. Areas of high vessel size, which were calculated on MRI, correspond with areas of high PET uptake, showing good correspondence between two different image modalities.

3.6 Other Applications.

FIG. 13A through FIG. 13D, and FIG. 14A and FIG. 14B illustrate by way of example and not limitation, additional applications for the disclosed technology.

Figure 14A:
FIG. 14A and FIG. 14B are images of gradient and spin echo for determining fMRI as generated in response to a quadruple echo gradient and spin echo EPI sequence according to an embodiment of the present disclosure.
Figure 14B:
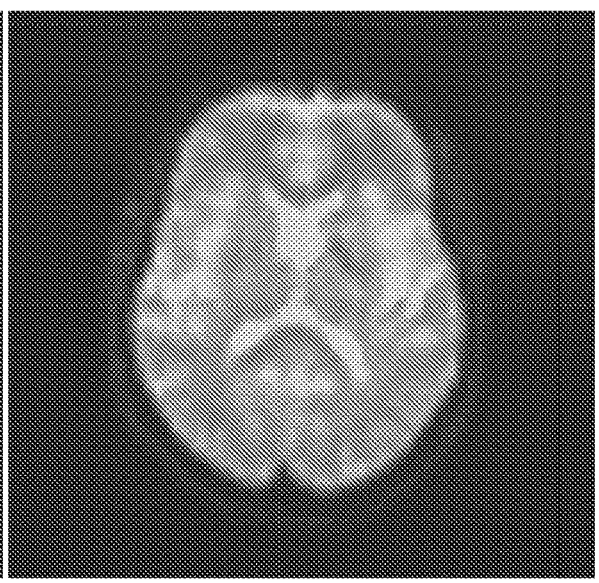

In addition to brain tumors, with the disclosed quadruple echo gradient and spin echo EPI sequence it is possible to image stroke, which relies on perfusion and vessel size index markers, spinal cord, in which perfusion has never before been accomplished (FIG. 13A through FIG. 13D), and fMRI (FIG. 14A and FIG. 14B).

In FIG. 13A through FIG. 13C show spinal cord perfusion with T2 weighted images seen from three different perspectives, similarly FIG. 13D through FIG. 13F shows Echo 1 from these same three perspectives.

In FIG. 14A gradient echo image is seen alongside a spin echo image in FIG. 14B. It will be noted that a conventional gradient-echo fMRI (FIG. 14A) suffers from signal dropout in the orbitofrontal region (arrow), thus the use of a spin echo fMRI, which does not have the same dropout issue, would help supplement the gradient echo fMRI findings.

4. System Block Diagram.

Figure 15:
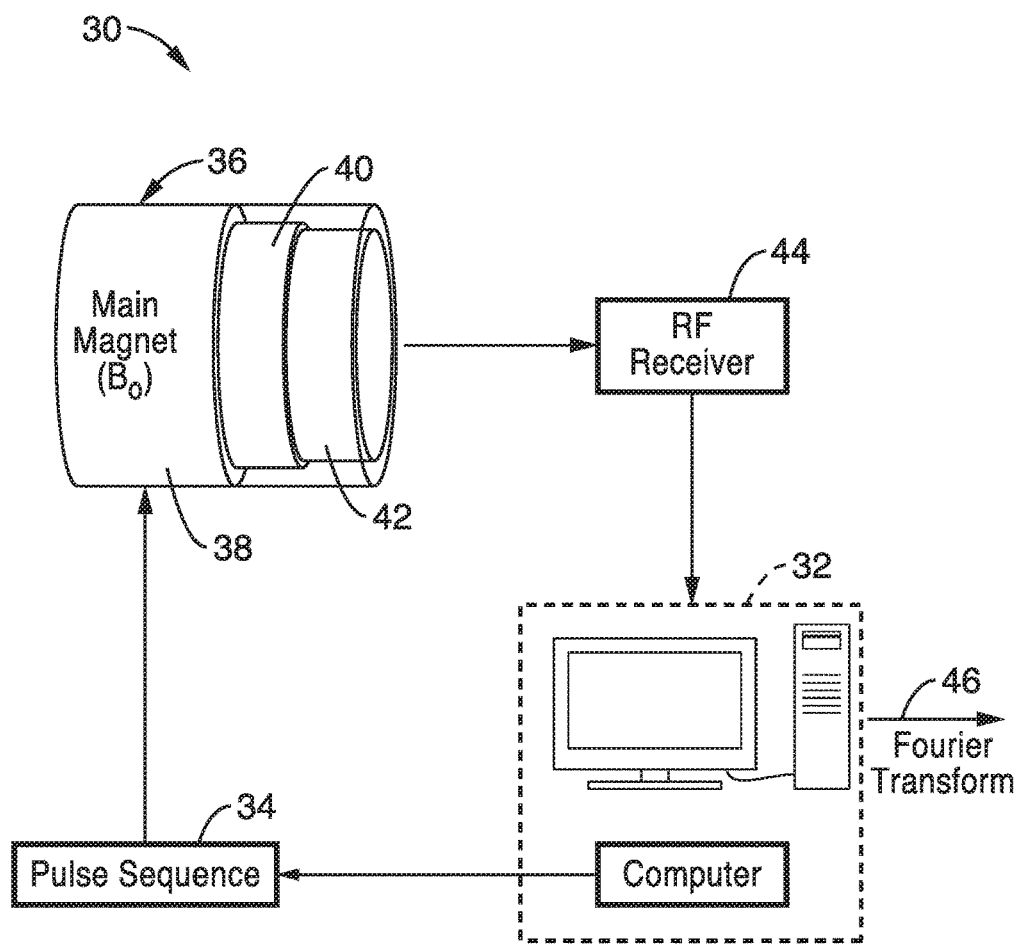
FIG. 15 is a block diagram of a quadruple echo gradient and spin echo EPI sequence apparatus according to an embodiment of the present disclosure.
Figure 16A:
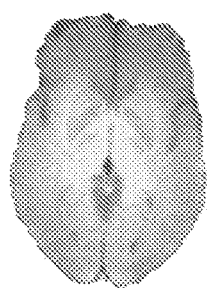
FIG. 16A through FIG. 16D are echo images generated in response to the quadruple echo gradient and spin echo EPI sequence apparatus shown in FIG. 15.
Figure 16B:
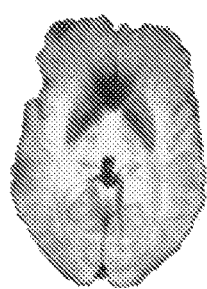
Figure 16C:
Figure 16D:
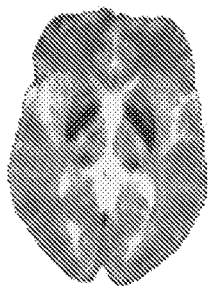

FIG. 15 illustrates a block diagram of an embodiment 30 for generating the disclosed quadruple echo gradient and spin echo EPI sequence. A computer processor and memory 32 are configured with programming for generating pulse sequences 34, directed to a magnetic imaging device 36 and its main magnet 38 ($B_0$), RF coil 40 ($B_1$), and gradient coils ($G_x$, $G_y$, $G_z$). For the sake of clarity of illustration the target is not shown, however, one of ordinary skill in the art will appreciate that the target is located within the area of all three sets of magnets (38, 40, 42) and the receiver 44. It should be appreciated that after interacting with the target, the RF signals are received by an RF receiver 44, with echoes processed by the programming of the computer process and memory 32. It should be appreciated that a number of processors may be utilized, as desired.

FIG. 16A through FIG. 16D depict Echo 1 through Echo 4 images generated in response to a Fourier transform performed in FIG. 15.

Figure 17:
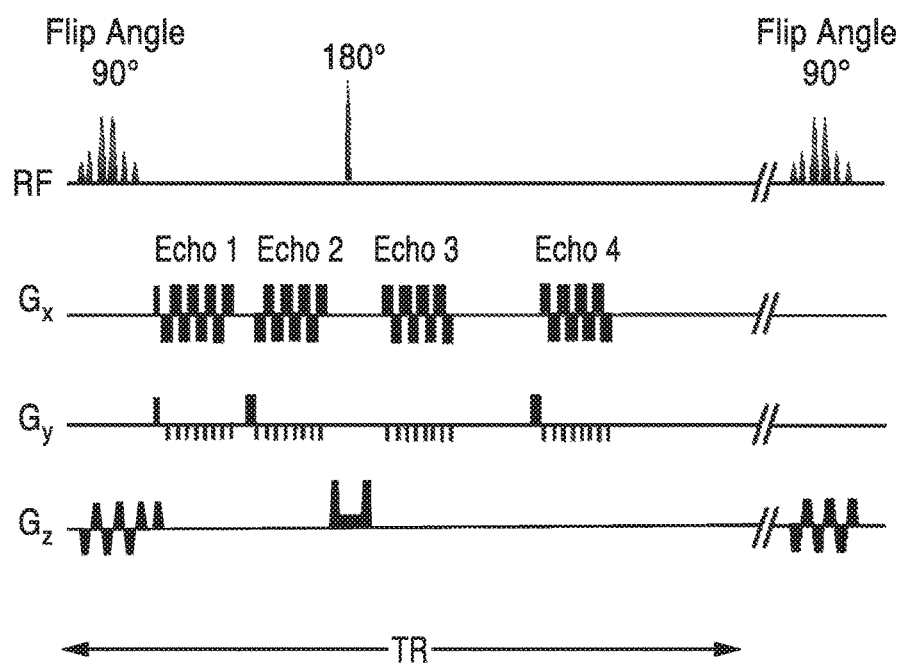
FIG. 17 is a waveform diagram showing waveforms for RF and $G_x$, $G_y$, $G_z$ coils being generated by the quadruple echo gradient and spin echo EPI sequence apparatus shown in FIG. 15.

FIG. 17 illustrates an example pulse sequence for the RF coil along with the $G_x$, $G_y$, $G_z$ coils.

The enhancements described in the presented technology can be readily implemented within various RF and gradient imaging system, primarily in regard to medical diagnostic images and in particular MRI and similar systems. It should also be appreciated that these systems are preferably implemented to include one or more computer processor devices (e.g., CPU, microprocessor, microcontroller, computer enabled ASIC, etc.) and associated memory storing instructions (e.g., RAM, DRAM, NVRAM, FLASH, computer readable media, etc.) whereby programming (instructions) stored in the memory are executed on the processor to perform the steps of the various process methods described herein. The presented technology is non-limiting with regard to memory and computer-readable media, insofar as these are non-transitory, and thus not constituting a transitory electronic signal.

Embodiments of the present technology may be described herein with reference to flowchart illustrations of methods and systems according to embodiments of the technology, and/or procedures, algorithms, steps, operations, formulae, or other computational depictions, which may also be implemented as computer program products. In this regard, each block or step of a flowchart, and combinations of blocks (and/or steps) in a flowchart, as well as any procedure, algorithm, step, operation, formula, or computational depiction can be implemented by various means, such as hardware, firmware, and/or software including one or more computer program instructions embodied in computer-readable program code. As will be appreciated, any such computer program instructions may be executed by one or more computer processors, including without limitation a general purpose computer or special purpose computer, or other programmable processing apparatus to produce a machine, such that the computer program instructions which execute on the computer processor(s) or other programmable processing apparatus create means for implementing the function(s) specified.

Accordingly, blocks of the flowcharts, and procedures, algorithms, steps, operations, formulae, or computational depictions described herein support combinations of means for performing the specified function(s), combinations of steps for performing the specified function(s), and computer program instructions, such as embodied in computer-readable program code logic means, for performing the specified function(s). It will also be understood that each block of the flowchart illustrations, as well as any procedures, algorithms, steps, operations, formulae, or computational depictions and combinations thereof described herein, can be implemented by special purpose hardware-based computer systems which perform the specified function(s) or step(s), or combinations of special purpose hardware and computer-readable program code.

Furthermore, these computer program instructions, such as embodied in computer-readable program code, may also be stored in one or more computer-readable memory or memory devices that can direct a computer processor or other programmable processing apparatus to function in a particular manner, such that the instructions stored in the computer-readable memory or memory devices produce an article of manufacture including instruction means which implement the function specified in the block(s) of the flowchart(s). The computer program instructions may also be executed by a computer processor or other programmable processing apparatus to cause a series of operational steps to be performed on the computer processor or other programmable processing apparatus to produce a computer-implemented process such that the instructions which execute on the computer processor or other programmable processing apparatus provide steps for implementing the functions specified in the block(s) of the flowchart(s), procedure (s) algorithm(s), step(s), operation(s), formula(e), or computational depiction(s).

It will further be appreciated that the terms "programming" or "program executable" as used herein refer to one or more instructions that can be executed by one or more computer processors to perform one or more functions as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors.

It will further be appreciated that as used herein, that the terms processor, computer processor, central processing unit (CPU), and computer are used synonymously to denote a device capable of executing the instructions and communicating with input/output interfaces and/or peripheral devices, and that the terms processor, computer processor, CPU, and computer are intended to encompass single or multiple devices, single core and multicore devices, and variations thereof.

From the description herein, it will be appreciated that that the present disclosure encompasses multiple embodiments which include, but are not limited to, the following:

1. A method of performing echo-planar imaging, comprising: (a) generating a quadruple echo gradient and spin echo echo-planar imaging pulse sequence for a magnetic resonance imaging (MRI) system configured for generating MRI images of a patient in response to receiving and processing RF signals; (b) wherein said quadruple echo gradient and spin echo echo-planar imaging pulse sequence is generated as two echo trains between an excitation pulse (90°) and a refocusing pulse (180°) to achieve two gradient echo images as T2*-weighted images; (c) wherein said quadruple echo gradient and spin echo echo-planar imaging pulse sequence is generated with one echo train directly after the 180° pulse, leading to asymmetric spin echo images as T2'-weighted images; and (d) wherein a last echo train generates spin echo images as T2-weighted images.

2. The method of any preceding embodiment, wherein signals received from each scan performed with said quadruple echo gradient and spin echo echo-planar imaging pulse sequence results in generation of four images, each having different contrasts.

3. The method of any preceding embodiment, wherein said quadruple echo gradient and spin echo echo-planar imaging pulse sequence is configured for driving a radio frequency coil, and magnetic resonance gradient coils within the MRI system.

4. The method of any preceding embodiment, wherein said magnetic resonance gradient coils comprise Gx, Gy, and Gz gradient coils.

5. The method of any preceding embodiment, wherein said quadruple echo gradient and spin echo echo-planar imaging pulse sequence is generated at field strengths of approximately 3 T (Tesla).

6. The method of any preceding embodiment, wherein obtaining four simultaneous and differently-weighted images allows determining of conditions requiring solving relationships of up to four unknowns.

7. The method of any preceding embodiment, further comprising measuring hypoxia (R2') in brain tumors in response to determining quantitative T2 and T2* measures, wherein four unknowns are solved in response to analyzing four differently-weighted images acquired simultaneously.

8. The method of any preceding embodiment, further comprising determining relative oxygen extraction fraction (rOEF) in response to dividing R2' by relative cerebral blood volume (rCBV).

9. The method of any preceding embodiment, further comprising determining a forward transfer coefficient, $K_{trans}$, as a biomarker that is related to the permeability of the vasculature in brain tumors wherein receipt of four echoes allows for determining a baseline T1-weighted image ($S_0$) that can be combined with a T1 map and two-compartment pharmacokinetic modeling of contrast agent exchange.

10. The method of any preceding embodiment, further comprising determining mean vessel diameter, vessel density and vessel size for brain tumors in response to simultaneous acquisition of gradient echo and spin echo EPI sequences.

11. A method of performing echo-planar imaging, comprising: (a) generating a quadruple echo gradient and spin echo echo-planar imaging pulse sequence for a magnetic resonance imaging (MRI) system configured for generating MRI images of a patient in response to receiving and processing RF signals; (b) driving a radio frequency coil and magnetic resonance gradient coils with said quadruple echo gradient and spin echo echo-planar imaging pulse sequence within the MRI system; (c) wherein signals received from each scan performed with said quadruple echo gradient and spin echo echo-planar imaging pulse sequence results in generation of four images, each having different contrasts; (d) wherein said quadruple echo gradient and spin echo echo-planar imaging pulse sequence is generated as two echo trains between an excitation pulse (90°) and a refocusing pulse (180°) to achieve two gradient echo images as T2*-weighted images); (d) wherein said quadruple echo gradient and spin echo echo-planar imaging pulse sequence is generated with one echo train directly after the 180° pulse, leading to asymmetric spin echo images as T2'-weighted images; and (e) wherein a last echo train generates spin echo images as T2-weighted images.

12. The method of any preceding embodiment, wherein said magnetic resonance gradient coils comprise Gx, Gy, and Gz gradient coils.

13. The method of any preceding embodiment, wherein said quadruple echo gradient and spin echo echo-planar imaging pulse sequence is generated at field strengths of approximately 3 T (Tesla).

14. The method of any preceding embodiment, wherein obtaining four simultaneous and differently-weighted images allows determining of conditions requiring solving relationships of up to four unknowns.

15. The method of any preceding embodiment, further comprising measuring hypoxia (R2') in brain tumors in response to determining quantitative T2 and T2* measures, wherein four unknowns are solved in response to analyzing four differently-weighted images acquired simultaneously.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

TABLE 1

| Sequence Parameter Table | |
|---|---|
| Sequence Parameter | Value |
| Parallel Imaging Reduction Factor | 3 |
| Matrix size ($k_x \times k_y$) | 128 × 104 |
| Number of Slices | 19 |
| Slice Thickness | 5 mm |
| TR | 2000 mS |

What is claimed is:

1. A method of performing echo-planar imaging, comprising:
   generating a quadruple echo gradient and spin echo echo-planar imaging pulse sequence, comprising a total of four echo trains, for a magnetic resonance imaging (MRI) system configured for generating MRI images of a patient in response to receiving and processing RF signals, wherein an MRI image generated by the MRI system using the quadruple echo gradient and spin echo echo-planar imaging pulse sequence has an in-plane resolution with reduced voxel size based on the four echo trains;
   wherein said quadruple echo gradient and spin echo echo-planar imaging pulse sequence is generated as two echo trains between a 90 degrees excitation pulse and a 180 degrees refocusing pulse to achieve two gradient echo images as T2*-weighted images and two echo trains after the 180° pulse;
   wherein the two echo trains after the 180° pulse of said quadruple echo gradient and spin echo echo-planar imaging pulse sequence are generated with one echo train directly after the 180° pulse, leading to asymmetric spin echo images as T2'-weighted images, and a last echo train of the four echo trains that generates spin echo images as T2-weighted images.

2. The method as recited in claim 1, wherein signals received from each scan performed with said quadruple echo gradient and spin echo echo-planar imaging pulse sequence results in generation of four images, each having different contrasts.

3. The method as recited in claim 1, wherein said quadruple echo gradient and spin echo echo-planar imaging pulse sequence is configured for driving a radio frequency coil, and magnetic resonance gradient coils within the MRI system.

4. The method as recited in claim 1, wherein said magnetic resonance gradient coils comprise Gx, Gy, and Gz gradient coils.

5. The method as recited in claim 1, wherein said quadruple echo gradient and spin echo echo-planar imaging pulse sequence is generated at field strengths of 3 T (Tesla).

6. The method as recited in claim 1, wherein obtaining four simultaneous and differently-weighted images allows determining of conditions requiring solving relationships of up to four unknowns.

7. The method as recited in claim 1, further comprising measuring hypoxia (R2') in brain tumors in response to determining quantitative T2 and T2* measures, wherein four unknowns are solved in response to analyzing four differently-weighted images acquired simultaneously.

8. The method as recited in claim 7, further comprising determining relative oxygen extraction fraction (rOEF) in response to dividing R2' by relative cerebral blood volume (rCBV).

9. The method as recited in claim 1, further comprising determining a forward transfer coefficient $K_{trans}$, a biomarker that is related to the permeability of the vasculature in brain tumors, by determining a baseline T1-weighted image ($S_0$) and combining the image $S_0$ with a T1 map and two-compartment pharmacokinetic modeling of contrast agent exchange.

10. The method as recited in claim 1, further comprising determining mean vessel diameter, vessel density and vessel size for brain tumors in response to simultaneous acquisition of gradient echo and spin echo EPI sequences.

11. A method of performing echo-planar imaging, comprising:

generating a quadruple echo gradient and spin echo echo-planar imaging pulse sequence, comprising a total of four echo trains, for a magnetic resonance imaging (MRI) system configured for generating MRI images of a patient in response to receiving and processing RF signals;

driving a radio frequency coil and magnetic resonance gradient coils with said quadruple echo gradient and spin echo echo-planar imaging pulse sequence within the MRI system;

wherein signals received from each scan performed with said quadruple echo gradient and spin echo echo-planar imaging pulse sequence results in generation of four images, each having different contrasts, and an in-plane resolution with a reduced voxel size based on the four echo trains;

wherein said quadruple echo gradient and spin echo echo-planar imaging pulse sequence is generated as two echo trains between a 90 degrees excitation pulse and a 180 degrees refocusing pulse to achieve two gradient echo images as T2*-weighted images and two echo trains after the 180° pulse;

wherein the two echo trains after the 180° pulse of said quadruple echo gradient and spin echo echo-planar imaging pulse sequence are generated with one echo train directly after the 180° pulse, leading to asymmetric spin echo images as T2'-weighted images, and a last echo train of the four echo trains that generates spin echo images as T2-weighted images.

12. The method as recited in claim 11, wherein said magnetic resonance gradient coils comprise Gx, Gy, and Gz gradient coils.

13. The method as recited in claim 11, wherein said quadruple echo gradient and spin echo echo-planar imaging pulse sequence is generated at field strengths of 3 T (Tesla).

14. The method as recited in claim 11, wherein obtaining four simultaneous and differently-weighted images allows determining of conditions requiring solving relationships of up to four unknowns.

15. The method as recited in claim 11, further comprising measuring hypoxia (R2') in brain tumors in response to determining quantitative T2 and T2* measures, wherein four unknowns are solved in response to analyzing four differently-weighted images acquired simultaneously.

\* \* \* \* \*